United States Patent [19]

Stuart

[11] Patent Number: 4,462,250

[45] Date of Patent: Jul. 31, 1984

[54] GRAIN MOISTURE METER

[76] Inventor: John A. Stuart, Box 11, Grandview, Manitoba, Canada, R0L 0Y0

[21] Appl. No.: 321,436

[22] Filed: Nov. 16, 1981

[51] Int. Cl.³ .............................................. G01N 27/22
[52] U.S. Cl. ..................................... 73/73; 324/61 R
[58] Field of Search ................. 73/73, 1 R; 324/61 P, 324/61 R; 374/1

[56] References Cited

U.S. PATENT DOCUMENTS

| | | | |
|---|---|---|---|
| 2,613,249 | 10/1952 | Babb | 73/73 |
| 3,146,617 | 9/1964 | Klein | 324/61 P |
| 3,293,907 | 12/1966 | Schnatz | 73/73 |

FOREIGN PATENT DOCUMENTS 1119251  3/1982  Canada ................................ 73/73

*Primary Examiner*—Charles Frankfort
*Assistant Examiner*—Denis E. Corr

[57] ABSTRACT

A grain moisture meter and/or a meter for measuring grain bin temperatures, comprises a half-wave pulse oscillator with pulses connecting to the outer shell of a grain container. Pulses pass through the grain and through a central electrode and the signals are amplified and fed to a meter to read the moisture content. A thermistor is in circuit to adjust for variations in temperature of the grain. The device can be adjusted to test grain by three methods. Firstly, it can given an indication of dryness, toughness and dampness to a farmer in the field when combining. Secondly, by use of charts or graphs, it can be used to identify each point on the scale giving an accurate determination of the moisture content of any grade above number four grade and thirdly, by the use of other charts or graphs, accurate readings of any grain grade can be ascertained.

9 Claims, 3 Drawing Figures

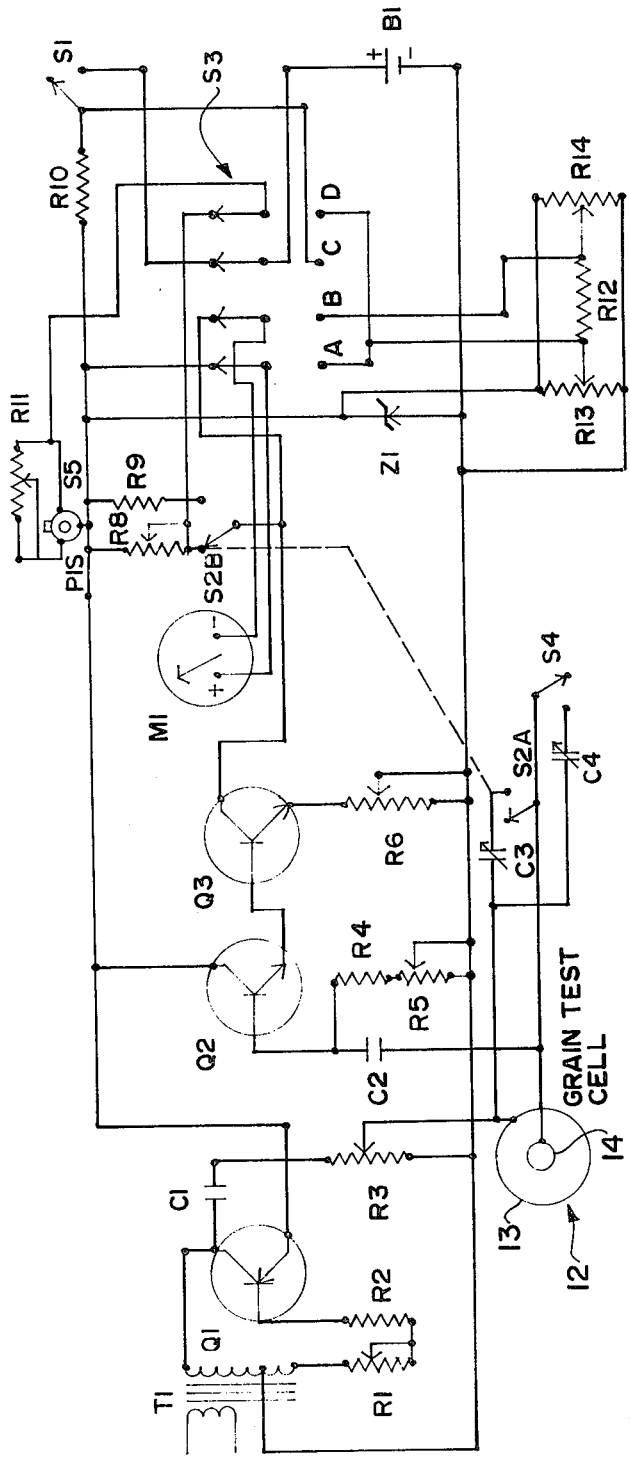

4,462,250

GRAIN MOISTURE METER

BACKGROUND OF THE INVENTION

This invention relates to new and useful improvements in grain moisture indicators. Conventionally, such indicators can only be used to give an approximate moisture content, particularly portable indicators which are adapted for use in the field.

Such grain moisture indicators or meters are unsatisfactory for general use because the accuracy is limited primarily due to the frequencies involved and also due to the difficulty in adjusting for temperature variations of the grain within the test cell.

SUMMARY OF THE INVENTION

This invention overcomes these disadvantages by the provision of a meter which is extremely accurate and portable and which can be calibrated for use under varying conditions.

One aspect of the invention is to provide a grain moisture indicator for use with a grain cell which includes an outer shell and a central element insulated from said outer shell, and a source of electrical power; comprising in combination a half-wave pulse oscillator operatively connected to said outer shell, signal amplifying means operatively connected to said central element and meter means operatively connected to said amplifier means.

Another aspect of the invention may utilize the thermistor to adjust for the temperature variations of the grain.

A still further aspect of the invention includes means to calibrate the instrument for various uses such as grain bin temperature readings, types of grain and grades of grain.

A still further aspect of the invention is to provide a device of the character herewithin described which is simple in construction, economical in manufacture and otherwise well suited to the purpose for which it is designed.

With the foregoing in view, and other advantages as will become apparent to those skilled in the art to which this invention relates as this specification proceeds, the invention is herein described by reference to the accompanying drawings forming a part hereof, which includes a description of the preferred typical embodiment of the principles of the present invention, in which:

DESCRIPTION OF THE DRAWINGS

FIG. 2 is a schematic wiring diagram of the circuit of the device.

In the drawing like characters of reference indicate corresponding parts in the different figures.

DETAILED DESCRIPTION

Figure 1:
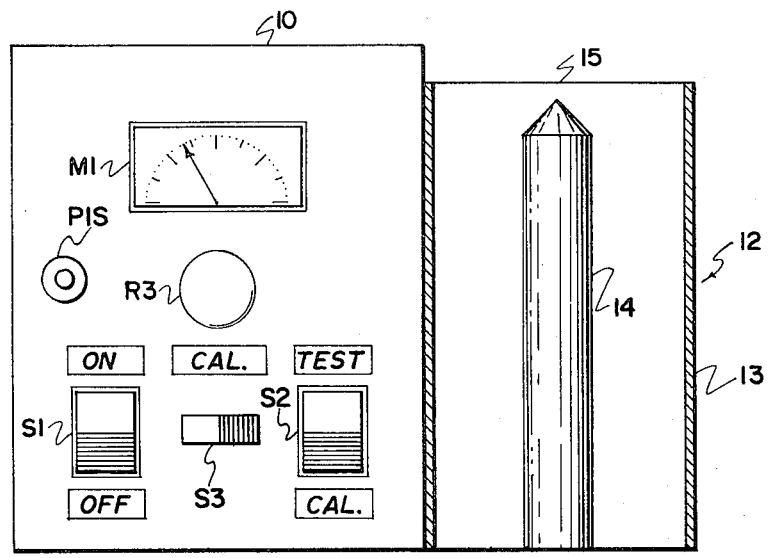
FIG. 1 is a partially schematic, partially sectioned front elevation of the device showing the grain cell and casing as an integral unit.

Proceeding therefore to describe the invention in detail, reference character 10 illustrates a casing which includes the source of electrical energy in the form of a battery B1 (FIG. 2) together with a grain cell collectively designated 12 connected to one side of the casing by any conventional means (not illustrated).

The grain cell consists of an outer container or shell 13 with a central electrode 14 electrically insulated therefrom and extending upwardly towards the open upper end 15 thereof and a measured amount of grain (not illustrated) may be poured into the cell for moisture measurement purposes.

The front of the casing displays an indicator or meter M1, a calibrating knob R3, a main ON-OFF switch S1; S3 and P1S, and a test/calibrating switch S2.

Dealing next with the circuitry shown in FIG. 2, battery B1 is preferably a 9-volt battery or alternatively a 9-volt regulated power supply which is conventional although different voltages may be utilized.

T1 illustrates a center tapped transformer together with resistors R1 and R2 with both sides of the circuitry being connected to a transistor Q1 thus forming a half-wave pulse oscillator and a choice of components operates the transistor to produce pulses in the range of 11,000 to 12,000 cycles per second which is the preferable range of frequency.

This circuitry also provides or forms a spike oscillator.

The pulse signal is fed through condenser C1 to a variable resistor R3 and thence to the outer shell 13 of the grain cell or container 12.

R3 is a voltage divider and is used to calibrate the instrument so that the correct amount of pulse signal passes through the grain container.

The signal passing through the grain within the container then passes through the condenser C2 to the input of amplifier transistors Q2 and Q3 with resistor R4 acting as a buffer resistor to prevent overload of transistor Q2. R5 is used to calibrate the lower end of the meter scale.

Transistors Q2 and Q3 amplify the signal in order to get sufficient deflection to operate the meter M1 to which the transistors are operatively connected as clearly shown.

Meter M1 will therefore give the deflection to indicate the moisture content of grain and also to calibrate the instrument.

The aforementioned thermistor R7 (which will hereinafter be described), when S3 is in the grain test position, is connected across the meter M1 and is situated in the grain sample that is to be tested, to control the correct amount of power necessary to keep the meter reading in moisture content of the grain so that there is the correct moisture content reading at different temperatures of the grain within the test cell.

Resistor R8 also across the meter M1 and parallel with R7, may be variable or fixed at a given value in order to calibrate the thermistor R7.

A variable resistor R6 is situated between transistor Q3 and the negative side of the circuit and may be used to compensate for differences in characteristics of transistors Q2 and Q3 so that numerous instruments can be calibrated to the same chart or graph.

Switch S1 is provided on the positive side of the circuit to switch the instrument ON and OFF for grain testing. Switch S2 is a double-pole, double-throw switch used to calibrate the instrument in one position and to test grain in the other position.

Switch S2 is provided with two switches, namely S2A and S2B. When switch S2 is in the "calibrate" position, switch S2A switches the condenser C3 into the circuit to act as a dummy load condenser to simulate grain in the test cell when calibrating the instrument to test grain and this variable condenser C3 is adjusted to a specific value for calibrating the instrument.

Switch S2B at the same time as above, changes the shunt resistors in the meter M1 circuit from R8 and R7 to a shunt resistor R9. The reason for R9 is that R7 cannot remain in the circuit while calibrating as it will change value with ambient temperature changes and would therefore impair the calibrating function.

C4 and S4 are used on damp grain models only to calibrate the unit for testing high moisture grains (i.e. corn at 45% moisture content).

R10 in conjunction with Z1, a zener diode, make up a voltage regulator to hold the operating voltage constant.

Figure 3:
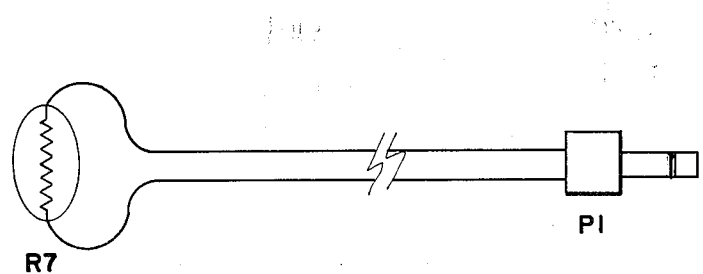
FIG. 3 is a schematic view of the temperature sensor and plug.

R11 is a variable resistor calibrated so that the thermometer reads 20° C. when the temperature sensor plug P1 is removed from the sensor plug socket P1S. This plug is operatively connected to the grain temperature sensor R7 by means of a flexible electric cable (preferably coaxial) (see FIG. 3) and which may take the form of a thermistor or thermometer.

R12 is used to hold the thermometer readings linear.

R13 and R14 are variable and are used to calibrate the thermometer.

S3, which is a 4 pole double throw-switch, performs four switching functions, namely S3A, S3B, S3C and S3D. The letters A, B, C, D indicate the individual switches in FIG. 2.

S3A switches the positive side of the meter from the grain testing position to the temperature position.

S3B switches the negative side of the meter from the grain testing position to the temperature position.

S3C switches the battery from the input terminal of S1 to the output terminal of S1 so that the temperature reading is immediately on the meter.

S3D switches the temperature sensor socket connection from the grain testing position to temperature position. This switch is a push botton type switch normally in the position shown in FIG. 2. When depressed, the termperature may be read on M1.

P1S is the temperature plug socket, which includes S5.

S5 switches from R11 to temperature sensor R7 by inserting a temperature sensor plug P1 into P1S.

When temperature sensor plug is out of P1S, S5 connects R11 into the temperature sensor circuit, and is used to test the battery.

When the temperature sensor plug is in P1S, the temperature at the temperature sensor R7 can be read directly off the meter scale.

Therefore, numerous temperature sensors can be placed in each grain bin full of grain with separate sensor plugs on each so that an operator can plug each individual plug into the temperature testing unit, take the temperature of the grain in each individual grain bin, and keep a record of the temperature in each individual bin of grain.

The instrument can be calibrated to test grain by three methods.

Firstly, and perhaps more importantly, the grain cell is filled to capacity with loose grain and the test is made to deflect the meter which not only can be marked in the usual way, but can also have indicators so that the operator knows that below a given point on the meter scale, the grain is tested to read DRY. Between this first given point and a second given point on the scale, the indication will be that the grain is tough and above the second point, the indication is that the grain is in the damp range.

This is a most important facility for a farmer operating a combine who wishes to know the condition of the grain during the combining or prior to the combining operation.

In other words, the cut-off point between dry grain and tough grain is approximately 14.5% moisture and between tough grain and damp grain, is between 14.5% and 17% moisture.

With the circuitry illustrated and the values of components as given, these readings are accurate within 5/10 of 1% with grain grade above number four. Other grains have different cut-off points.

The second method is to fill the grain container to capacity with loose grain and then test using charts or graphs to identify each point of the meter scale to indicate moisture content. This is accurate within 5/10 of 1% with grain grade above number four.

The third method is to weigh the grain with an accurate scale and using a dump funnel to dump the grain into the cell evenly with the same amount of compaction every time for an accurate reading of 0.1% for any grain grade at the factory and less than 0.3% out in the field.

This unit can also test grain by continuous flow for use on a combine, dryers, elevators, etc., and can be used for monitoring the change in moisture content in a grain bin.

As mentioned previously, the grain container or grain cell can be either a square or round container with a central electrode or metal tube in the center insulated from the outer container. The signal is fed to the outer shell and the amount of signal that passes through the grain is received by the central electrode connected to the input of Q2 through C2.

Preferably, the inside of the container is covered with lacquer or the like to prevent direct contact with the grain. When testing grain in the grain cell, temperature sensor R7 may be inserted into the grain sample from which the grain is transferred to the test cell thus controlling the correct amount of power as hereinbefore described and with the switch S3 in the grain testing position.

Finally, reference to FIG. 1 will show the socket for P1S on the casing which incorporates switch S5.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

I claim:

1. A grain moisture indicator comprising a grain cell having two terminals comprising an outer shell and a central element electrically insulated from the shell and arranged such that grain introduced into the cell provides an electrical path between said outer shell and said central element, a half-wave pulse oscillator having an output lead thereof connected to a load, means for connecting said one of the terminals to said load whereby the grain in said cell alters the load applied to the oscillator, signal amplifying means connected to the other terminal whereby the output of said oscillator is amplified and meter means for measuring the amplified output, a thermistor for insertion into the grain being tested and operatively connected across said meter to adjust the readings thereof relative to the temperature of the grain being tested within said cell, and means to calibrate said indicator, said means including a shunt resistor and a dummy load capacitor, and a two-position switch firstly to connect said shunt resistor across said meter, and to disconnect said thermistor from said meter and to connect said dummy load capacitor into parallel circuit with said amplifier means, when in one position, and secondly to disconnect said shunt resistor and re-connect said thermistor, and to disconnect said dummy load capacitor when in the other position.

2. The indicator according to claim 1 which includes a casing for said indicator and said source of electrical power, said grain cell being connected to one side of said casing to form a one-piece portable instrument.

3. The indicator according to claim 1 which includes means to selectively connect an external temperature sensing means to said indicator, said means including a temperature sensor plug socket operatively connected to said circuit and means to switch said indicator from a grain testing mode to a temperature sensing mode and vice-versa.

4. The indicator according to claim 3 in which said means also includes a temperature sensing device operatively connected to said plug socket.

5. The indicator according to claim 3 in which said meter includes a positive side and a negative side operatively connected to said source of electrical power, said means to switch said indicator including switch means to switch the positive and negative sides of said meter and the temperature sensing plug socket from the grain testing position to the temperature sensing position, and vice-versa.

6. The indicator according to claim 5 which includes an ON-OFF switch including an input terminal and an output terminal, operatively extending between said source of electrical power and said circuit, said last mentioned switch means switching the source of electrical power from the input terminal to the output terminal when said external temperature sensing means is operatively connected to said circuit whereby the temperature indicated by said external temperature sensing means is displayed directly and immediately on said meter.

7. The indicator according to claim 1 which includes means in said circuit for calibrating said indicator for use with the testing of relatively high moisture grain, said last mentioned means including a variable capacitor and means to switch said variable capacitor into and out of parallel connection with said grain cell.

8. The indicator according to claim 1 which includes means in said circuit for calibrating said indicator for use with the testing of relatively high moisture grain, said last mentioned means including a variable capacitor and means to switch said variable capacitor into and out of parallel connection with said grain cell.

9. The indicator according to claim 1 which includes means in said circuit for calibrating said indicator for use with the testing or relatively high moisture grain, said last mentioned means including a variable capacitor and means to switch said variable capacitor into and out of parallel connection with said grain cell.

* * * * *